(12) United States Patent
Chou

(10) Patent No.: US 6,622,781 B2
(45) Date of Patent: Sep. 23, 2003

(54) PAD

(75) Inventor: Chao-Mu Chou, Taipei (TW)

(73) Assignees: Ching-Yu Chou, Taipei (TW); Shiu-Yin Cheng, Taoyuan Hsien (TW)

(*) Notice: Subject to any disclaimer, the term of this patent is extended or adjusted under 35 U.S.C. 154(b) by 0 days.

(21) Appl. No.: 09/904,856

(22) Filed: Jul. 16, 2001

(65) Prior Publication Data

US 2002/0185258 A1 Dec. 12, 2002

(30) Foreign Application Priority Data

Jun. 6, 2001 (TW) .................................... 90209382 U

(51) Int. Cl.[7] .................................................. F28F 7/00
(52) U.S. Cl. .......................... 165/46; 607/96; 607/108; 607/114; 5/421; 5/655.5
(58) Field of Search .............................. 165/46; 607/96, 607/108, 114; 5/421, 655.5, 909

(56) References Cited

U.S. PATENT DOCUMENTS

| | | | | |
|---|---|---|---|---|
| 640,534 A | * | 1/1900 | Cheney | 165/46 |
| 3,874,504 A | * | 4/1975 | Verakas | 206/219 |
| 3,885,403 A | * | 5/1975 | Spencer | 165/46 |
| 3,951,127 A | * | 4/1976 | Watson et al. | 126/206 |
| 4,370,768 A | * | 2/1983 | Saloff | 5/682 |
| 5,150,707 A | * | 9/1992 | Anderson | 128/402 |
| 5,366,491 A | * | 11/1994 | Ingram et al. | 165/46 |
| 5,415,222 A | * | 5/1995 | Colvin et al. | 165/46 |
| 5,445,858 A | * | 8/1995 | Nwoko | 428/71 |
| 5,496,358 A | * | 3/1996 | Rosenwald | 607/108 |
| 6,024,761 A | * | 2/2000 | Barone et al. | 607/108 |
| 6,065,529 A | * | 5/2000 | Antoniuk et al. | 165/46 |
| 6,298,907 B1 | * | 10/2001 | Colvin et al. | 165/46 |

FOREIGN PATENT DOCUMENTS

| | | | | |
|---|---|---|---|---|
| DE | 3327212 A1 | * | 11/1984 | 165/46 |
| EP | 0059581 A2 | * | 9/1982 | 165/46 |

* cited by examiner

*Primary Examiner*—Terrell McKinnon
(74) *Attorney, Agent, or Firm*—Troxell Law Office PLLC

(57) ABSTRACT

A pad comprises a bag, an inner lining, a specific volume of liquid. The bag provides an inner space after being sealed. The inner lining is made of three dimensional textile with a size corresponding to the inner space of the bag so as to be inserted into the bag. The specific volume of liquid is poured into the bag.

5 Claims, 3 Drawing Sheets

PAD

BACKGROUND OF THE INVENTION

1. Field of the Invention

The present invention relates to pad, and, more particularly, to a heat dissipated pad without being deformed during being exerted a vertical load.

2. Description of Related Art

It is known that a pad is frequently used in different situations such as a seat pad, a sleep pad, a pillow pad, and etc. Of course, the pads in different situations offer different purposes such as cushioning, keeping warm, or dissipating heat.

The conventional pad mostly has an outerbag filled with padding such as sponge, soft textile, or the like. Alternatively, the outer bag is made of water-proof material and filled with liquid.

Although the conventional pad can offer a basic function thereof, it still gets involved in a deficiency to be overcome. The deficiency is in that the pad itself is a support element so that a deformation may result from the volume of the padding being equivalent with the size of the outer bag in case of the conventional pad being subjected to a load. Thus, the pad may move outward to result in a sunken part surrounded by a raised part. If the volume of the padding is much less than the size of the outer bag, the pad becomes flattened and loses the function thereof.

In fact, the inner lining of the conventional pad provides an additional function of heat transfer except the function of support such that the pad may become hardened after being compressed and loses the original effect of cushioning and relieving pressure.

SUMMARY OF THE INVENTION

An object of the present invention is to provide a pad, in which an inner lining of three dimensional textile is filled with certain amount of liquid and a gross volume of the inner lining, the liquid, and a resident air is less than the inner space of the pad to prevent the pad from deformation and keep the pad cool effectively.

BRIEF DESCRIPTION OF THE DRAWINGS

The present invention can be more fully understood by referencing to the following description and accompanying drawings, in which.

DETAILED DESCRIPTION OF THE PREFERRED EMBODIMENTS

Figure 1:
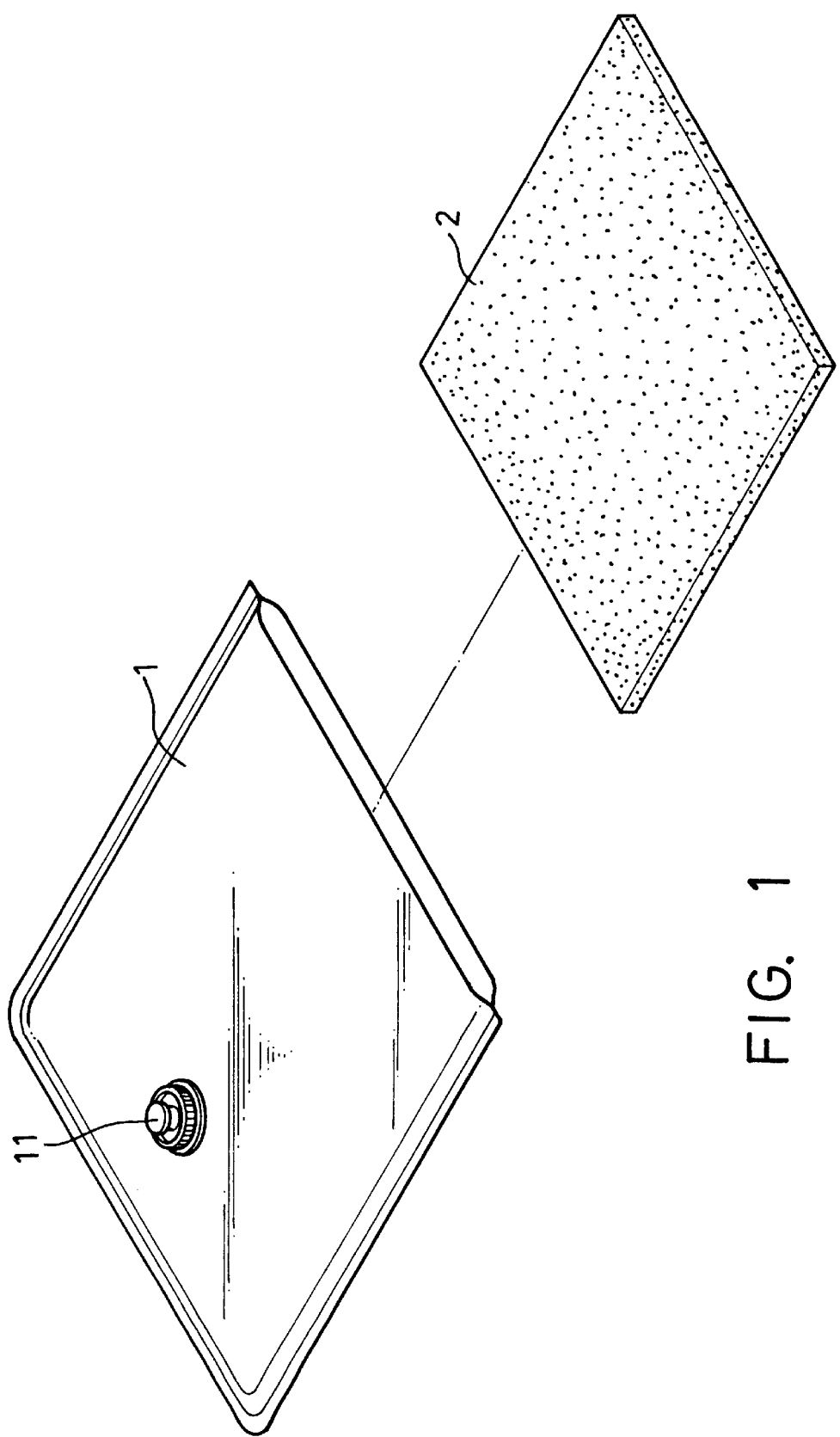
FIG. 1 is an exploded perspective view of a pad according to the present invention.
Figure 2:
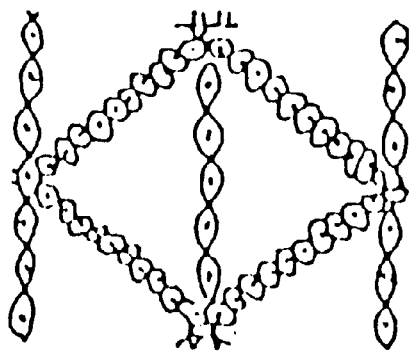
FIG. 2 is a sectional view of a three dimensional textile in the pad of the present invention.
Figure 2:
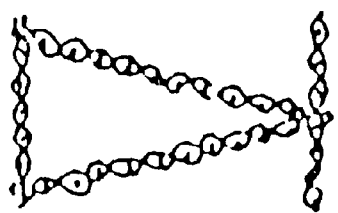
Figure 2:
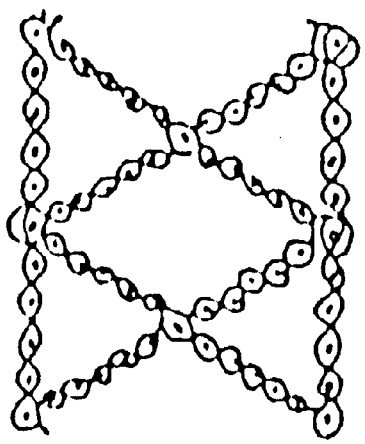
Figure 2:
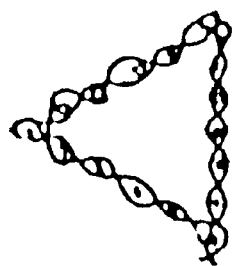
Figure 3:
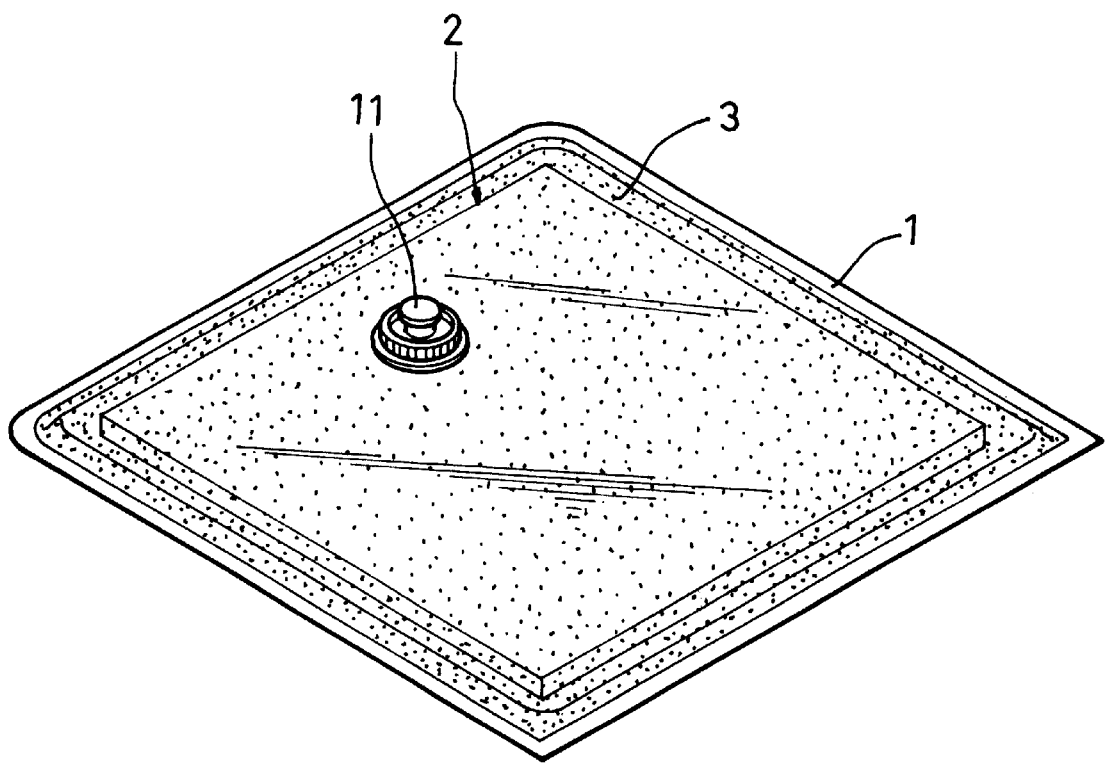
FIG. 3 is a perspective view of the pad according to the present invention after assembling.

Referring to FIGS. 1 to 3, a pad according to the present invention comprises a bag 1, an inner lining 2, and liquid 3.

Wherein, the bag 1 is for receiving the inner lining 2 and the liquid 3 so that the bag 1 is made of water resistant material. In order to admit the inner lining 2, the bag 1 has an open end and the open end is sealed after containing the inner lining 2 and the liquid 3. A valve 11 is attached to the bag 1 for taking out the air therein and injecting the liquid 3 so that it is possible for the valve 11 to be opened. Because this is a known art, no detail will be described further.

The inner lining 2 is made from a three dimensional textile and the size thereof is corresponding to the bag 1 so as to be received in the bag 1. The three dimensional textile has a plurality of upright fiber structures with a spacing room as shown in FIG. 2. The three dimensional textile is available in the market as the product made by The Japanese Dee-Rein Company.

The liquid 3 may be plain water or other liquid such as oil, or grease, and the liquid 3 is for guiding the heat. The gross volume of the liquid 3, the resident air, and the inner lining is less than the inner space offered by the bag 1. Furthermore, the liquid 3 can be added with an additive such as anti-freeze solution to avoid a phenomenon of being frozen.

Referring to FIGS. 1 to 3 again, the air in the bag 1 is removed after the inner lining 2 of the three dimensional textile being inserted into and the liquid 3 being poured into the bag 1. Thus, the bag 1 is sealed as soon as the bag 1 obtains a shape with a height corresponding to the three dimensional textile. In case of having the valve 11, the resident air can be discharged from the valve 11 and the liquid 3 can be injected through the valve 11. The finished product of the pad according to the present invention is illustrated in FIG. 3.

While the pad of the present invention is in use, the upright fiber structures on the three dimensional textile may support the vertical load exerted by the weight of a human body so that the inner lining 2 may not be squeezed to deform and expand outward. Thus, the weight of the human body can be supported evenly to achieve an effect of being pressurized evenly and pressure releasing. The liquid 3 can dissipate the heat generating from contacting with human body.

Moreover, the pad is in a state of vacuum as soon as the resident air is discharged so that the liquid can be distributed in accordance with the inner lining of the three dimensional textile without flowing. The feature provides that the liquid in the pad of the present invention can keep the original distribution in spite of the pad being disposed at different levels. That is, part of the pad can be disposed horizontally as a seat pad or a sleep pad and another part thereof can be raised uprightly as a leaning pad or a pillow pad. Thus, the effect of cushion and heat dissipation for the pad can be enhanced greatly.

It is appreciated from the preceding detail description that the pad of the present invention can support the weight of the human body completely to overcome the puzzle with regard to the non-forced part being deformed after subjecting a load. The user can feel cool while the pad of the present invention contacts with the body of the user due to the generated heat being dissipated by the liquid. These advantages are not possible for the conventional pad to reach effectively.

While the invention has been described with reference to preferred embodiment thereof, it is to be understood that modifications or variations may be easily made without departing from the spirit of this invention, which is defined in the appended claims.

What is claimed is:

1. A pad for supporting a human body comprising:

a) a bag bounding a sealed inner space;

b) an inner lining located in the inner space and configured to support a human body without outward expansion, the inner lining including a three dimensional textile having upper and lower spaced apart layers interconnected by a plurality of fiber structures extending at an acute angle with respect to each other; and, c) a predetermined quantity of liquid in the inner space whereby a gross volume of the liquid and the inner lining is less than a volume of the inner space to prevent deformation of the pad and to maintain cooling of the pad.

2. The pad of claim 1 wherein the liquid is water.
3. The pad of claim 1 wherein the liquid is oil.
4. The pad of claim 1 wherein the liquid is grease.
5. The pad of claim 1 wherein the liquid is an anti-freeze solution.

* * * * *